(12) United States Patent
Bullock et al.

(10) Patent No.: US 6,555,717 B2
(45) Date of Patent: Apr. 29, 2003

(54) CATALYTIC DEHYDROXYLATION OF DIOLS AND POLYOLS

(75) Inventors: R. Morris Bullock, Wading River, NY (US); Marcel Schlaf, Guelph (CA); Paul Joseph Fagan, Wilmington, DE (US); Elisabeth M. Hauptman, Wilmington, DE (US)

(73) Assignees: E. I. du Pont de Nemours and Company, Wilmington, DE (US); Brookhaven Science Associates, Upton, NY (US)

( * ) Notice: Subject to any disclaimer, the term of this patent is extended or adjusted under 35 U.S.C. 154(b) by 0 days.

(21) Appl. No.: 09/885,824

(22) Filed: Jun. 20, 2001

(65) Prior Publication Data

US 2002/0077511 A1 Jun. 20, 2002

Related U.S. Application Data

(60) Provisional application No. 60/212,778, filed on Jun. 20, 2000.

(51) Int. Cl.$^7$ .............................................. C07C 41/09
(52) U.S. Cl. ....................... 568/619; 568/698; 568/799; 568/861; 568/903; 502/152; 502/161
(58) Field of Search ................................ 568/619, 698, 568/799, 861, 903; 502/152, 161

(56) References Cited

U.S. PATENT DOCUMENTS

| | | |
|---|---|---|
| 5,276,181 A | 1/1994 | Casale et al. |
| 5,426,249 A | 6/1995 | Haas et al. |
| 5,543,379 A | 8/1996 | Gubitosa et al. |
| 5,600,028 A | 2/1997 | Gubitosa et al. |

FOREIGN PATENT DOCUMENTS

| EP | 0 523 014 | 1/1993 |
|---|---|---|

OTHER PUBLICATIONS

Halcrow et al., Tris–pyrazolyl–borate Dihydrogen Complexes of Ruthenium, J. Chem. Soc. Commun., Issue 5, Mar. 1993, pp. 465–467.*

Hill et al., Polyazolyl Chelate Chemistry: Organometallic Dihydridobis(pyrazol–1–yl)borato Complexes of Ruthenium (II), Organometallics, vol. 17, No. 19, Sep. 1998, pp. 4249–4258.*

Consuelo Vicente, Reduction of ketones by dihydrogen or hydrogen transfer catalysed by a ruthenium complex of the hydridotris (3,5–dimethyl) pyrazolyl borate ligand, Journal of Molecular Catalysis A: Chemical, vol. 98, No. 1 (1995), pp. L5–L8, Toulouse Cedex, France.

Richard Baltzly, Catalytic Debenzylation. The Effect of Substitution on the Strength of the O–Benzyl and N–Benzyl Linkages, Journal of the American Chemical Society, Volumber 65, No. 10, Chem. Soc. 1307 (Oct. 1943), pp. 1984–1992.

Chemical Abstracts, vol. 47, No. 6, (Mar. 1953) Columbus Ohio, Abstract No. 2963h.

Braca, Giuseppe, Galletti, Anna Marie Raspolli and Sbrana, Glauco; Journal of Organometallic Chemistry. 1991, 417 41–49.

Chin, Mitchell S., Heinekey, D. Michael, Payne, Neil G. and Sofield, Chadwick D. ; Organometallics 1989, 8 1824–1826.

O'hare, D., Green, Jennifer C., Marder, T., Collins, S., Stringer, G., Kakkar, Ashok K., Kaltsoyannis, N., Kuhn, A., Lewis, R., Mehnert, C., Scoot, P., Kurmoo, M. and Pugh, S. ; Organometallics 1992, 11, 48–55.

Chin, Mitchell S. and Heinekey, D. Michael; J. Am. Chem. Soc. 1990, 112, 5166–5175.

Ovchinnikov, Maxim V. and Angelici, Robert J. ; J. Am. Chem. Soc. 2000, 122, 6130–6131.

Venier, Clifford G. and Casserly, Edward W. ; J. Am. Chem. Soc. 1990, 112, 2808–2809.

Williams, R. A., Tesh, Kris F. and Hanusa, Timothy P. ; J. Am. Chem. Soc. 1991, 113, 4843–4851.

Delville–Desbois, M.H., Mross, S. and Astruc, D. ; Organometallics 1996, 15, 5598–5604.

Frankcom, Tracy M., Green, Jennifer C., Nagy, A., Kakkar, Ashok K. and Marder, Todd B. ; Organometallics 1993, 12, 3688–3697.

Eisenstadt, A. , Frolow, F. and Efraty, A., J. Chem. Soc., Chem. Commun., 1982 642–643.

Miyamoto, T. Ken, Tsutsui, Minoru and Chen, Li–Ban ; The Chemistry Society of Japan, Chemistry Letters, pp. 729–730, 1981.

Stasunik, Andrea and Malisch, Wolfgang ; Journal of Organometallic Chemistry, 270, 1984, C56–C62.

Fagan, Paul J., Mahoney, Wayne S., Calabrese, Joseph C. and Williams, Ian D. ; American Chemical Society 1990, 9, 1843–1852.

Chinn, Mitchell S. and Heinekey, D. Michael ; J. Am. Chem. Soc. 1987, 109, 5856–5867.

\* cited by examiner

*Primary Examiner*—Rosalynd Keys
(74) *Attorney, Agent, or Firm*—Inna Y. Belopolsky

(57) ABSTRACT

Secondary alcohols, specifically diols and polyols, are dehydroxylated to the corresponding primary alcohols using a homogeneous organometallic ruthenium complex catalyst.

11 Claims, 1 Drawing Sheet

CATALYTIC DEHYDROXYLATION OF DIOLS AND POLYOLS

This application claims benefit of Provisional Application No. 60/212,778, filed Jun. 20, 2000.

FIELD OF INVENTION

Organometallic ruthenium complexes are catalysts for the homogeneous catalytic dehydroxylation of secondary alcohols, specifically diols and polyols, to the corresponding primary alcohols using $H_2$ gas as the stoichiometric reductant.

BACKGROUND

Alcohols, diols and polyols are industrial compounds that are widely used as polymer monomers, solvents, and reactants for organic synthesis. One method for the preparation of these compounds is through the dehydroxylation of polyols and diols to the corresponding diols and alcohols.

Ruthenium metal is well known as a catalyst for the dehydroxylation of polyols and diols to the corresponding diols and alcohols (U.S. Pat. Nos. 5,426,249 and 5,543,379). However, ruthenium metal as a catalyst shows little or no selectivity between secondary and primary alcohols.

Braca, et al., (*J. Organomet. Chem.* 1991, 417, 41–49) reported on the use of a ruthenium complex, $[Ru(CO)_3I_3]^-$, for the dehydroxylation of glycerol and other polyols. This dehydroxylation reaction has distinct disadvantages. First, hydrogen gas and carbon monoxide were used under harsh reactive conditions. Secondly, in addition to the desired dehydroxylation products, various byproducts were obtained in significant amounts.

Chinn et al., (*Organometallics* 1989, 8, 1824–1826) described the synthesis and spectroscopic properties of the unstable dihydrogen complex $[Cp^*Ru(CO)_2(H_2)]^+$ which was found to decompose to $\{[Cp^*Ru(CO)_2]_2(\mu\text{-H})\}^+OTf^-$. No catalytic activity of either of these complexes is mentioned.

The present process for the selective dehydroxylation of diols to their corresponding primary alcohols avoids many of the foregoing disadvantages and has the advantages of mild reaction conditions, the absence of expensive, oxygen-sensitive ligands (such as triaryl phosphines, trialkyl phosphines) and nitrogen-based ligands in the catalytic system, and tolerance to acid and water. Furthermore, the process exhibits high regioselectivity, resulting in the nearly exclusive formation of terminal primary alcohols and $\alpha,\omega$-diol or their ethers as the final hydrogenated reaction products.

SUMMARY OF THE INVENTION

The invention is directed to a process for the selective dehydroxylation of a secondary alcohol, comprising: contacting the secondary alcohol with hydrogen in the presence of a catalytically effective amount of a catalyst precursor having the formula $\{[CpRu(CO)_2]_2(\mu\text{-H})\}^+Q^-$ or $\{[CpRu(CO)(PR'_3)]_2(\mu\text{-H})\}^+Q^-$ or $\{[ZRu(L)]_2(\mu\text{-H})\}^+Q^-$, wherein $Q^-$ is a non-coordinating or weakly coordinating nonreactive anion; Cp is $\eta^5$—$C_5R_5$ wherein R is selected from the group consisting of hydrogen and substituted and unsubstituted $C_1$—$C_{18}$ alkyl groups, where any two adjacent R groups can together form a ring; R' is selected from the group consisting of hydrogen, alkyl, aryl, alkoxy and aryloxy; Z is hydridotris(3,5-dimethylpyrazolyl)borate or hydrocarbyl hydridotris(3,5-dimethylpyrazolyl)borate; L is $(CO)_2$ or COD; and COD is 1,5-cyclooctadiene.

Preferably, the secondary alcohol additionally contains a primary alcohol functionality. Most preferred is where the secondary alcohol is selected from the group consisting of 1,2-propanediol, glycerol and 1-phenyl-1,2-ethanediol.

In a preferred embodiment, $Q^-$ is $OSO_2CF_3^-$ or $BF_4^-$, and R is hydrogen, methyl, i-propyl, benzyl, dimethylsilyl, or together with the cyclopentadienyl group forms an indenyl ring; R' is methyl, phenoxy, p-fluorophenyl, or cyclohexyl; and Z is hydridotris(3,5-dimethylpyrazolyl)borate.

Another embodiment additionally comprises the presence of added $H^+Q^-$, preferably HOTf. In another embodiment, added $H^+Q^-$ is not present and the secondary alcohol has an aryl group on the carbon containing the secondary alcohol functionality.

DRAWINGS

DETAILED DESCRIPTION OF THE INVENTION

Figure 1:
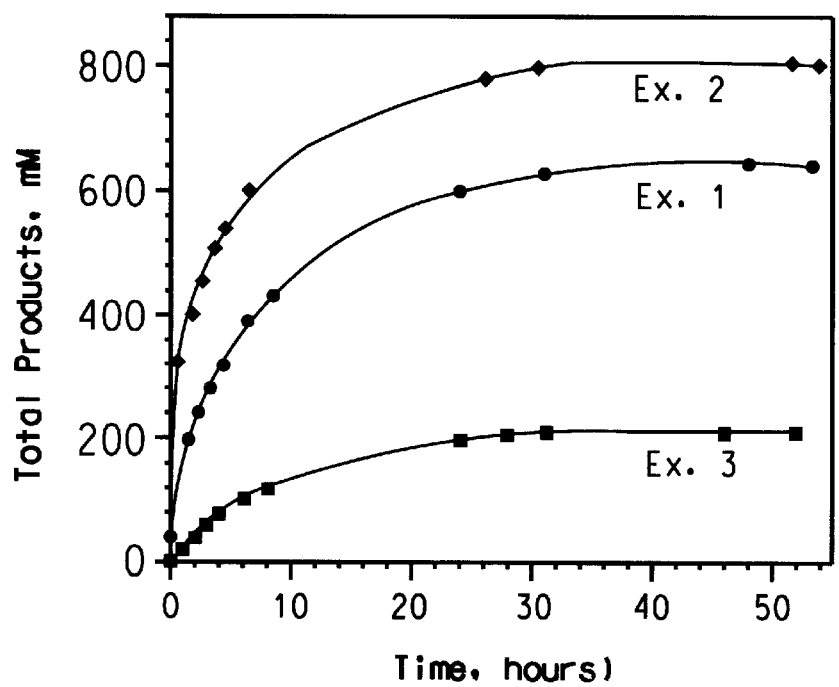
FIG. 1 is a graph showing the time of reaction vs. concentration of HOTf.

In the present description, "alkyl" means an alkyl group comprising from 1 to 18 carbon atoms. Common examples of such alkyl groups include methyl, ethyl, propyl, isopropyl, butyl, s-butyl, isobutyl, pentyl, neopentyl, hexyl, heptyl, isoheptyl, 2-ethylhexyl, cyclohexyl and octyl. The alkyl group may be linear, branched, or cyclic.

By "hydrocarbyl" is meant a monovalent group containing only carbon and hydrogen, and may be chiral or achiral. Unless otherwise stated, it is preferred that hydrocarbyl (and substituted hydrocarbyl) groups contain 1 to 30 carbon atoms.

By "substituted" is meant that a compound or functional group contains one or more substituent groups that do not cause the compound to be unstable or unsuitable for the use or reaction intended, and are inert under reaction conditions. Substituent groups which are generally useful include nitrile, ether, ester, halo, amino (including primary, secondary and tertiary amino), hydroxy, oxo, vinylidene and substituted vinylidene, carboxyl, silyl and substituted silyl, nitro, sulfinyl, and thioether. Highly basic substituents are generally not suitable in the process of present invention unless they are previously protonated with acid or protected with a suitable protecting group.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can be mono-, di-, or trisubstituted with, e.g., halogen, lower alkyl, lower alkoxy, lower alkylthio, trifluoromethyl, lower acyloxy, aryl, heteroaryl, and hydroxy. By "aryl" is also meant heteroaryl groups where heteroaryl is defined as a 5-, 6-, or 7-membered aromatic ring system having at least one atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl. The heteroaryl groups can themselves be substituted with halogen, lower alkyl, lower alkoxy, lower alkylthio, trifluoromethyl, lower acyloxy, aryl, heteroaryl, and hydroxy.

The following definitions are used herein:
Ar'=3,5-bis(trifluoromethyl)phenyl
Bz=benzyl
COD=1,5-cyclooctadiene
Cp*=$\eta^5$—$C_5Me_5$
Cy*=cyclohexyl
HOTf=$CF_3SO_3H$
$Pr^i$=iso-propyl
Me=methyl
OTf=$OSO_2CF_3$
OTf=$OSO_2CF_3$—
pz=pyrazolyl
Tp*=hydridotris(3,5-dimethylpyrazolyl)borate The present invention provides a process for the selective dehydroxylation of a secondary alcohol in the presence of a homogeneous ruthenium catalyst precursor. The catalyst precursor is of the formula $\{[CpRu(CO)_2]_2(\mu\text{-H})\}^+Q^-$ or $\{[CpRu(CO)(PR'_3)]_2(\mu\text{-H})\}^+Q^-$ or $\{[ZRu(L)]_2(\mu\text{-H})\}^+Q^-$, wherein $Q^-$ is a non-coordinating or weakly coordinating nonreactive anion; Cp is $\eta^5$—$C_5R_5$ wherein R is selected from the group consisting of hydrogen and substituted and unsubstituted $C_1$—$C_{18}$ alkyl groups, where any two adjacent R groups can together form a ring; R' is selected from the group consisting of hydrogen, alkyl, aryl, alkoxy and aryloxy; Z is hydridotris(3,5-dimethylpyrazolyl)borate or hydrocarbyl hydridotris(3,5-dimethylpyrazolyl)borate; L is $(CO)_2$ or COD; and COD is 1,5-cyclooctadiene.

By "secondary alcohol" is meant a compound containing a secondary alcohol functional group. A secondary alcohol may contain additional alcohol functional groups, as well as other types of functionalities.

Weakly coordinating anions are known to those skilled in the art. Such anions are often bulky anions, particularly those that may delocalize their negative charge. The coordinating capability of such anions has been discussed in the literature; see, for instance, W. Beck et al., *Chem. Rev.*, vol. 88, p. 1405–1421 (1988), and S. H. Strauss, *Chem. Rev.*, Vol. 93, p. 927–942 (1993). Weakly coordinating anions suitable for the processes of the present invention include $OSO_2CF_3$—(herein abbreviated as $OTf^-$), $SO_4^{2-}$, $HSO_4$—, $BF_4$—, $PF_6$—, $SbF_6$—, $BPh_4$—, and $BAr'_4$— where Ar'=3, 5-bis(trifluoromethyl)phenyl. Most preferred is OTf.

The catalytically active species for the present invention is believed to be proton (or H+) and $[CpM(CO)_2]H$ in combination with one or both of the transient complexes $[CpM(CO)_2(\eta^2\text{-H}_2)]+$ and $[CpM(CO)_2]^+$, all of which are generated or added under the reaction conditions. Any synthetic route may be used that leads to the same reactive species, such as use of $CpM(CO)_2OTf$, and $[CpM(CO)_2]_2$, $[CpM(CO)_2]_2(\mu\text{-H})^+$ or $CpM(CO)_2H$ in the presence of $H^+Q^-$ as catalyst precursors. The catalytic active species for the other catalysis precursors of the present invention, $\{[CpRu(CO)(PR'_3)]_2(\mu\text{-H})\}^+Q^-$ or $\{[ZRu(L)]_2(\mu\text{-H})\}^+Q^-$, are believed to be analogous. Similarly, any synthetic route that leads to the reactive species for these catalysis precursors may be used.

A preferred method of synthesis for the $\{[CpRu(CO)_2]_2(\mu\text{-H})\}^+OTf^-$ catalyst precursor is as follows: In a drybox, a flask was charged with $Cp^*Ru(CO)_2H$ (2.05 g, 6.986 mmol), prepared as described in Fagan et al., *Organomet.*, 1990, 9, 1843). The $Cp^*Ru(CO)_2H$ was dissolved in 2 ml of $CH_2Cl_2$. Triflic acid (310 μl, 3.5 mmol) was added slowly to the flask, resulting in vigorous gas evolution ($H_2$). Diethyl ether (10 ml) was then added and a yellow solid precipitated out of solution. The yellow solid was isolated by filtration and rinsed twice with a minimum amount of diethyl ether.

The preferred process includes the addition of the $H^+Q^-$ acid to the reaction mixture. Suitable acids include those with a pKa sufficient to protonate the secondary alcohol. An acid with a pKa of less than or equal to about 3 is generally sufficient. The preferred acid is HOTf. Another preferred process for alcohols with aryl groups attached to the carbon of the secondary alcohol group is without addition of the $H^+Q^-$ acid.

Suitable secondary alcohols for dehydroxylation in the present invention include, but are not limited to, the classes of linear, branched or cyclic saturated $C_2$–$C_{18}$ compounds. As discussed above, secondary alcohols may be substituted as defined above. Examples of suitable substituents include, but are not limited to, alkyl groups, aryl groups, vinyl groups, halogens, and hydroxy groups. The present invention is highly selective towards reduction of secondary alcohol functional groups, without concomitant reduction of the primary alcohol, forming α, ω-substituted alcohols such as 1,3-propanediol. Preferred secondary alcohols contain at least one primary alcohol functionality. Most preferred alcohols are $C_2$–$C_6$ saturated diols and polyols, which may be substituted with alkyl or aryl groups, including 1,2-propanediol, glycerol, and 1-phenyl-1,2-ethanediol.

The processes may be run neat or in a suitable solvent. Suitable solvents for the dehydroxylation reaction are non-coordinating, non-basic, inert and able to partially dissolve the catalyst precursor under reaction conditions. The solvents may be deuterated for ease of analysis. Preferred solvents are sulfolane (tetramethylene sulfone; tetrahydrothiophene-1,1-dioxide) and $CH_2Cl_2$.

The dehydroxylation reaction is carried out under an atmosphere of hydrogen gas or any mixture of hydrogen gas with other gases that do not interfere with the desired reaction, such as nitrogen, helium, neon and argon gases. Other in situ sources of hydrogen can also be used. The partial pressure of the hydrogen is about 14 to 1000 psi (0.1 to 7.0 MPa), preferably about 14 to 800 psi (0.1 to 5.5 MPa). The temperature range is about 80 to about 120° C., preferably about 100° C. to about 110° C. The temperature and pressure range can vary depending on the selection of solvent, providing the secondary alcohol and solvent remain in the liquid phase.

Materials and Methods

The compounds used are either commercially available or synthesized as described below, except for the following:

$\{[Cp^*Ru(CO)_2]_2(\mu\text{-H})\}^+$ $OTf^-$ was synthesized as described in Chinn, M. S.; et al., *Organometallics* 1989, 8, 1824–1826. $\{[CpRu(CO)_2]_2(\mu\text{-H})\}^+$ $OTf^-$ was synthesized as described in Stasunik, A.; et al., *J. Organomet. Chem.* 1984, 270, C56–C62. $CpRu(CO)(PMe_3)H$ and $CpRu(CO)(PCy_3)H$, were synthesized as described in Chinn, M. S.; et al., *J. Am. Chem. Soc.* 1990, 112, 5166–5175. $Tp^*Ru(COD)H$ and $Tp^*Ru(CO)_2H$ [$Tp^*$=$HB(pz^{Me_2})_3$, hydridotris(3,5-dimethylpyrazolyl)borate] were synthesized as described in Moreno, B.; et al., *J. Am. Chem. Soc.*, 1995; Vol. 117, pp 7441–7451. $\{(CpSiMe_2)_2Ru_2(CO)_4(\mu\text{-H})\}BF_4$ was synthesized as described in Ovchinnikov, M. V.; et al., *J. Am. Chem. Soc.* 2000, 122, 6130–6131. ($Cp^{Bu^t}_2$)H (tri-t-butylcyclopentadiene) was synthesized as described in Venier, C. G.; et al., *J. Am. Chem. Soc.* 1990, 112, 280814 2809. ($Cp^{Pr^i}_4$)H (tetra-i-propylcyclopentadiene) was synthesized as described in Williams, R. A.; et al., *J. Am. Chem. Soc.* 1991, 113, 4843–4851. ($Cp^{Bz}_5$)H (pentabenzylcyclopentadiene) was synthesized as described in Delville-Desbois, M. H.; et al., *Organometallics* 1996, 15, 5598–5604. [Ind(Me_3)]H (1,2,3-trimethylindene) was synthesized as described in Frankcom, T. et al., *Organometallics* 1993, 12, 3688–3697.

SYNTHESIS OF $(Cp^{Bu^t}{}_2)Ru(CO)_2H$

A mixture of $(Cp^{Bu^t}{}_2)H$ (0.300 g, 1.68 mmol) and $Ru_3(CO)_{12}$ (0.359 g, 0.561 mmol) was refluxed in heptane (ca. 30 mL) for ca. 5 hours. The extent of the reaction was monitored by recording the formation of the product $(Cp^{Bu^t}{}_2)Ru(CO)_2H$ by infrared spectroscopy [v(CO): bands at 2023 cm$^{-1}$ and 1964 cm$^{-1}$]. The solution was filtered and the solvent removed in vacuo to obtain $(Cp^{Bu^t}{}_2)Ru(CO)_2H$ as a dark red oil (>0.11 g, 63% pure as estimated by $^1$H NMR of the Bu$^t$ resonances in 12% estimated yield). [$^1$H NMR $(C_6D_6)$: δ1.01 (s 18 H C$\underline{Me}_3$); 4.97 (t, $^4J_{HH}$=2 Hz, 1H, $\underline{H}_3C_5{}^{Bu^t}{}_2$); 4.65 (d, $^4J_{HH}$=2 Hz, 2H, $\underline{H}_3C_5{}^{Bu^t}{}_2$); −10.42 (s 1 H Ru—$\underline{H}$). IR (hexane) v(CO): 2022 (s) cm$^{-1}$, 1963 (s) cm$^{-1}$].

SYNTHESIS OF $(Cp^{Pr^i}{}_4)Ru(CO)_2H$

A mixture of $(Cp^{Pr^i}{}_4)H$ (0.300 g, 1.28 mmol) and $Ru_3(CO)_{12}$ (0.273 g, 0.427 mmol) was refluxed in heptane (ca. 25 mL) for 9 hours and the extent of the reaction was monitored by IR spectroscopy. The color of the reaction mixture turned dark brown during the course of the reaction. The reaction mixture was filtered and the filtrate was pumped in vacuo to obtain a dark brown oil. The dark oil was dissolved in pentane and filtered though silica gel to obtain a clear yellow solution. It was finally pumped in vacuum to obtain a yellow oil which on cooling at −40° C. yielded $(Cp^{Pr^i}{}_4)Ru(CO)_2H$ as a yellow solid (0.226 g, 45%). [$^1$H NMR $(C_6D_6)$: δ 4.80 (s, 1H, $\underline{HC}_5{}^{Pr^i}{}_4$), 2.57 (sep, $^3J_{HH}$=7 Hz, 2H, C$\underline{H}Me_2$); 2.49 (sep, $^3J_{HH}$=7 Hz, 2H, C$\underline{H}Me_2$); 1.24 (d, $^3J_{HH}$=7 Hz, 6H, CH$\underline{Me}_2$); 1.18 (d, $^3J_{HH}$=7 Hz, 6H, CH$\underline{Me}_2$); 1.11 (d, $^3J_{HH}$=7 Hz, 6H, CH$\underline{Me}_2$); 0.94 (d, $^3J_{HH}$=7 Hz, 6H, CH$\underline{Me}_2$); −10.3 (s, 1H), Ru—$\underline{H}$). $^{13}$C NMR $(C_6D_6)$: δ 203.6 (d, $^2J_{CH}$=9 Hz, CO); 113.7 (s, Cp-ring-$\underline{C}$-Pr$^i$): 112.4 (s, Cp-ring-$\underline{C}$-Pr$^i$); 75.9 (dt, $^1J_{CH}$=171 Hz, $^2J_{CH}$=5 Hz, Cp-ring-$\underline{C}$H); 26.7 (q, $^1J_{CH}$=127 Hz, CH$\underline{Me}_2$); 26.2 (q, $^1J_{CH}$=126 Hz, CH$\underline{Me}_2$); 25.7 (d, $^1J_{CH}$=133 Hz, $\underline{C}$H$Me_2$); 25.5 (q, $^1J_{CH}$=126 Hz, CH$\underline{Me}_2$); 25.4 (d, $^1J_{CH}$=127 Hz, $\underline{C}$H$Me_2$); 25.2 (q, $^1J_{CH}$=126 Hz, CH$\underline{Me}_2$). IR (hexane) v(CO): 2015 (s) cm$^{-1}$, 1956 (s) cm$^{-1}$. Analysis Calculated for $C_{19}H_{30}O_2Ru$: C 58.27%; H 7.72%. Found: C 58.45%; H 7.67%].

SYNTHESIS OF $(Cp^{Bz}{}_5)Ru(CO)_2H$

A mixture of $(Cp^{Bz}{}_5)H$ (0.500 g, 0.969 mmol) and $Ru_3(CO)_{12}$ (0.207 g, 0.324 mmol) was refluxed in heptane (ca. 25 mL) for 10 days and the extent of the reaction was monitored by IR spectroscopy. The color of the reaction mixture turned brownish yellow during the course of the reaction. The reaction mixture was filtered through alumina and then solvent was removed in vacuo to obtain a dark brown oil. The brown oil was dissolved in pentane (ca. 5 mL) and kept at −30° C. until a brown oily solid precipitated out. The supernatant pentane extract was decanted and the solvent was removed in vacuo to obtain $(Cp^{Bz}{}_5)Ru(CO)_2H$, a yellow oily solid (0.154 g, 24%). $^1$H NMR $(C_6D_6)$: δ 7.02–6.87 (m, 25H, $C_6\underline{H}_5$), 3.61 (s, 10H, C$\underline{H}_2C_6H_5$), −9.92 (s, 1H, Ru—$\underline{H}$). IR (hexane) v(CO): 2020 (s) cm$^{-1}$, 1963 (s) cm$^{-1}$.

SYNTHESIS OF $\{[Ind(Me_3)]Ru(CO)_2\}_2$ $[Ind(Me_3)]H$ (0.300 g, 1.90 mmol) and $Ru_3(CO)_{12}$ (0.405 g, 0.633 mmol) was refluxed in methyl iso-butyl ketone (ca. 50 mL) for 4 hours during which the formation of a dark brown precipitate was observed. The extent of the reaction was monitored by $^1$H NMR spectroscopy. The reaction mixture was then concentrated to ca. 10 mL for further precipitation. The precipitate was isolated by filtration, followed by washing with hexane and then vacuum dried to obtain $\{[Ind(Me_3)]Ru(CO)_2\}_2$ as a brown solid (0.253 g, 42%). Further purification of the dimer can be obtained by Soxhlet extraction in toluene to obtain $\{[Ind(Me_3)]Ru(CO)_2\}_2$ as a yellow solid. [$^1$H NMR $(CD_2Cl_2)$: δ 7.18 (m, 2H, $C_6\underline{H}_4$-ring); 6.99 (m, 2H, $C_6\underline{H}_4$-ring); 2.09 (s, 3H, $\underline{Me}$ $C_5$-ring); 2.05 (s, 6H, two $\underline{Me}$ groups of $C_5$-ring). $^1$H NMR $(C_6D_6)$: δ7.06 (m, 2H, $C_6\underline{H}_4$-ring); 6.83 (m, 2H, $C_6\underline{H}_4$-ring); 1.85 (s, 3H, $\underline{Me}$ $C_5$-ring); 1.82 (s, 6H, two $\underline{Me}$ groups of $C_5$-ring). $^{13}$C NMR $(CD_2Cl_2)$: δ 126.0 (dd, $^1J_{CH}$=162 Hz, $^2J_{CH}$=7 Hz, 2C, $\underline{C}_6H_4$-ring); 119.0 (dd, $^1J_{CH}$=167 Hz, $^2J_{CH}$=6 Hz, 2C, $\underline{C}_6$-ring); 109.1 (s, 1C, $\underline{C}_5$-ring); 108.5 (s, 2C, $\underline{C}_5$-ring); 95.8 (s, 2C, $\underline{C}_5$-ring); 10.2 (q, $^1J_{CH}$=128 Hz, 2C, two $\underline{Me}$ groups of $C_5$-ring); 9.3 (q, $^1J_{CH}$=128 Hz, 1C, $\underline{Me}$ $C_5$-ring). IR $(CH_2Cl_2)$ v(CO): 1941 and 1771 cm$^{-1}$].

SYNTHESIS OF $Cp^*Ru(CO)(PMe_3)H$ $PMe_3$ (0.250 g, 3.28 mmol) was added to a solution of $Cp^*Ru(CO)_2H$ (0.500 g, 1.70 mmol) in hexane (ca. 30 mL) and the reaction mixture was stirred at room temperature for 90 minutes. The solvent was then removed in vacuo to obtain an orange solid. The orange solid was vacuum sublimed at 30 mTorr and 60° C. to obtain $Cp^*Ru(CO)(PMe_3)H$ as a yellow solid (0.412 g, 71%). [$^1$H NMR $(CD_2Cl_2)$: 1.97 (d, $^4J_{HP}$=2 Hz, 15H, $C_5\underline{Me}_5$); 1.37 (d, $^2J_{HP}$=9 Hz, 9H, P$\underline{Me}_3$); −12.38 (d, $^2J_{HP}$=39 Hz, 1H, Ru—$\underline{H}$). $^{13}$C NMR $(CD_2Cl_2)$: δ 204.1 (dd, $^2J_{CH}$=9 Hz, $^2J_{CP}$=17 Hz, CO); 95.8 (d, $^2J_{CP}$=2 Hz, $\underline{C}_5Me_5$); 22.7 (dq, $^1J_{CH}$=128 Hz, $^1J_{CP}$=31 Hz, P$\underline{Me}_3$); 11.8 (q, $^1J_{CH}$=127 Hz, $C_5\underline{Me}_5$). $^{31}$P $\{^1H\}$ NMR $(CD_2Cl_2)$: δ 9.9 (s, $\underline{P}Me_3$). IR (hexane) v(CO): 1924 (br) cm$^{-1}$].

SYNTHESIS OF $CpRu(CO)[P(OPh)_3]H$

A mixture of CpH (9.00 mL, 109 mmol) and $Ru_3(CO)_{12}$ (0.900 g, 1.41 mmol) was refluxed in heptane (ca. 25 mL) for 4.5 hours. The color of the solution changed from dark orange to lemon yellow. At this point, an aliquot taken for infrared spectroscopy showed predominant formation of the dicarbonyl complex $CpRu(CO)_2H$ (2033 and 1973 cm$^{-1}$) along with the presence of minor amounts of $[CpRu(CO)_2]_2$ (1944 and 1793 cm$^{-1}$) and $\eta^4$—$(CpH)Ru(CO)_3$ (2064, 1998 and 1987 cm$^{-1}$). The reaction mixture was cooled to −78° C. and a solution of $P(OPh)_3$ (0.510 g, 1.65 mmol) in heptane (ca. 25 mL) was added to it over a period of 30 minutes. The reaction mixture was then stirred overnight at −78° C. The solvent was then removed in vacuo to obtain a yellow oil which was chromatographed inside dry box over silica gel and eluted with a mixed solvent [ether 5%: hexane 95%]. The first yellow band was collected and the solvent was removed to obtain a yellow oil. The yellow oil was washed with hexane (ca. 5 mL) when $CpRu(CO)[P(OPh)_3]H$ precipitated out as a a light yellow solid (0.087 g). The supernatant hexane solution was decanted and again left at −30° C. for further crystallization (0.135 g of microcrystals). The overall yield was 27% with respect to triphenylphosphite. [$^1$H NMR $(C_6D_6)$: δ 7.30 (d, $^3J_{HH}$=8 Hz, 6H, —$OC_6\underline{H}_5$ ortho H's); 7.03 (virtual triplet, $^3J_{HH}$=8 Hz, 6H, —$OC_6\underline{H}_5$ meta H's); 6.86 (t, $^3J_{HH}$=8 Hz, 3H, —$OC_6\underline{H}_5$ para H's); 4.43 (d, $^3J_{HP}$=1 Hz, 5H, $C_5\underline{H}_5$); −11.34 (d, $^2J_{HP}$=35 Hz, 1H, Ru—$\underline{H}$). $^{13}$C NMR $(C_6D_6)$: δ 204.1 (dd, $^2J_{CH}$=8 Hz, $^2J_{CP}$26 Hz, CO); 152.7 (d, $^2J_{CP}$=6 Hz, $\underline{C}$-1(ipso) of Ph); 129.8 (dd, $^1J_{CH}$=161 Hz, $^2J_{CH}$=8 Hz, m-$\underline{C}$ of Ph); 124.9 (dt, $^1J_{CH}$=163 Hz, $^2J_{CH}$=8 Hz, p-$\underline{C}$ of Ph); 122.6 (dd, $^1J_{CH}$=163 Hz, $^3J_{CP}$=5 Hz, o-$\underline{C}$ of Ph); 83.7 (dd, $^1J_{CH}$=177 Hz, $^2J_{CP}$=2 Hz, $\underline{C}$p). $^{31}$P NMR $(C_6D_6)$: δ 160.9 (d, $^2J_{PH}$=35 Hz). IR (hexane) v(CO):

1967 (br) cm$^{-1}$. Analysis Calculated for $C_{24}H_{21}O_4P_1Ru_1$: C 57.02%; H 4.19%. Found: C 57.65%; H 4.40%].

SYNTHESIS OF CpRu([P(OPh)$_3$]$_2$H

A mixture of CpH (5.00 mL, 60.6 mmol) and $Ru_3(CO)_{12}$ (0.450 g, 0.704 mmol) was refluxed in heptane (ca. 35 mL) for 3 hours. The color of the solution changed from dark orange to lemon yellow. The reaction mixture was cooled to room temperature and a solution of P(OPh)$_3$ (1.309 g, 4.22 mmol) in hexane (ca. 25 mL) was added to it. The reaction mixture was stirred at room temperature for one day. The solvent was then removed in vacuo to obtain a yellow oil which was chromatographed over silica gel and eluted with a mixed solvent [ether 5%: hexane 95%]. The first yellow band was collected in two fractions (ca. 100 mL each). CpRu([P(OPh)$_3$]$_2$H crystallized out as light yellow micro crystals from the 2$^{nd}$ fraction (0.458 g, 28%). Another batch of CpRu([P(OPh)$_3$]$_2$H, slightly contanimated with triphenylphosphite, could be obtained from the 1$^{st}$ fraction (0.370, 22%). [$^1$H NMR (C$_6$D$_6$): δ 7.36 (d, $^3J_{HH}$=8 Hz, 12H, —OC$_6$H$_5$ ortho H's); 7.04 (virtual triplet, $^3J_{HH}$=8 Hz, 12H, —OC$_6$H$_5$ meta H's); 6.87 (t, $^3J_{HH}$=8 Hz, 3H, —OC$_6$H$_5$ para H's); 4.27 (s, 5H, C$_5$H$_5$); −12.06 (t, $^2J_{HP}$=36 Hz, 1H, Ru—H). $^{13}$C NMR (C$_6$D$_6$): δ 153.2 (t, $^2J_{CP}$=3 Hz, C-1(ipso) of Ph); 129.5 (dd, $^1J_{CH}$=160 Hz, $^2J_{CH}$=9 Hz, m-C Ph); 124.0 (td, $^1J_{CH}$=162 Hz, $^2J_{CH}$=8 Hz, p-C of Ph); 122.4 (d, $^1J_{CH}$=160 Hz, o-C of Ph); 81.9 (d, $^1J_{CH}$=177 Hz, Cp). $^{31}$P NMR (C$_6$D$_6$): δ 155.7 (d, $^2J_{PH}$=36 Hz). Analysis Calculated for $C_{41}H_{36}O_6P_2Ru_1$: C 62.51%; H 4.61%. Found: C 62.70%; H 4.83%].

SYNTHESIS OF CpRu(CO)[P(Ph—F)$_3$]H

A mixture of CpH (5.00 mL, 60.6 mmol) and $Ru_3(CO)_{12}$ (0.450 g, 0.704 mmol) was refluxed in heptane (ca. 50 mL) for 4 hours. The color of the solution changed from dark orange to lemon yellow. At this point, an aliquot taken for infrared spectroscopy showed predominant formation of the dicarbonyl complex CpRu(CO)$_2$H (2033 and 1973 cm$^{-1}$) with the presence of minor amounts of [CpRu(CO)$_2$]$_2$ (1944 and 1793 cm$^{-1}$) and η$^4$—(CpH)Ru(CO)$_3$ (2064, 1998 and 1987 cm$^{-1}$). The reaction mixture was then cooled to room temperature followed by the addition of a solution of P(p-fluorophenyl)$_3$ (0.567 g, 1.48 mmol) in heptane (ca. 30 mL). The resultant mixture was stirred overnight at room temperature. The solvent was then removed in vacuo to obtain an orangish-yellow oil which was chromatographed over silica gel and eluted with a mixed solvent [ether 5%: hexane 95%]. The first yellow band was collected and the solvent was removed to obtain a yellow oil. The yellow oil was washed with hexane (ca. 3 mL) when CpRu(CO)[P(Ph—F)$_3$]H separated out as a light yellow micro-crystalline solid (0.070 g). The supernatant hexane solution was decanted and again left at −30° C. for further crystallization (0.270 g of micro-crystals). The overall yield was 45% with respect top-fluoro-triphenylphosphite. [$^1$H NMR (C$_6$D$_6$): δ7.34 (complex m, 6H, C$_6$H$_4$ ortho H's); 6.69 (virtual triplet, $^3J_{HH}$=8 Hz, 6H, C$_6$H$_4$ meta H's); 4.68 (s, 5H, C$_5$H$_5$); −11.17 (d, $^2J_{HP}$=33 Hz, 1H, Ru—H). $^{13}$C NMR (C$_6$D$_6$): δ 206.2 (dd, $^2J_{CH}$=9 Hz, $^2J_{CH}$=9 Hz, $^2J_{CP}$=18 Hz, CO); 163.9 (dd, $^1J_{CF}$=251 Hz, $^4J_{CP}$=2 Hz, p-C of C$_6$H$_4$F); 135.5 (ddm, $^1J_{CH}$=158 Hz, $^2J_{CP}$=22 Hz, $^3J_{CF}$=8 Hz, o-C of C$_6$H$_4$F); 134.9 (dd, $^1J_{CP}$=49 Hz, $^4J_{FC}$=3 Hz, C-1(ipso) of C$_6$H$_4$F); 115.3 (ddd, $^1J_{CH}$=165 Hz $^2J_{CF}$=32 Hz, $^3J_{CP}$=11 Hz, m-C of C$_6$H$_4$F); 83.7 (dm, $^1J_{CP}$=176 Hz, $^2J_{CP}$=1 Hz, Cp). $^{31}$P{$^1$H} NMR (C$_6$D$_6$): δ 66.5 (s). $^{19}$F{$^1$H} NMR (C$_6$D$_6$): δ −110.8 (d, $^5J_{PF}$=2 Hz). IR (hexane) ν(CO): 1940 (br) cm$^{-1}$ ].

EXAMPLES

For all examples, a set of standard conditions (described in this paragraph) were used for the systematic study of the catalytic dehydroxylation of 1,2-propanediol, 1-phenyl-1,2-ethanediol, and glycerol with {[Cp*Ru(CO)$_2$]$_2$(μ-H)}$^+$ OTf$^-$ in sulfolane. A sulfolane solution 1 M in 1,2-propanediol and 0.1 M in toluene (internal standard for gas chromatography (GC) analysis) was used with a reaction volume of 50 mL in a 300 mL glass-lined Parr Mini-Reactor which was stirred at 300 or 600 rpm. These conditions permitted the withdrawal of at least 5–10 samples of 0.5 mL each for analysis of the products of the reaction mixture as a function of time. Except where otherwise specified, the reaction temperature was 110° C., and hydrogen gas was fed at 750 psi (5.2 MPa) before heating. Concentration of added acid, CF$_3$SO$_3$H (HOTf), varied as specified in the descriptions of the individual reactions. The autoclave assembly was heated to the desired temperature using a Parr Model 4842 PID controller except in case of the (Cp$^{Bu^t}$$_2$)Ru(CO)$_2$H catalyst where a similar heater was used.

EXAMPLE 1

DEHYDROXYLATION OF 1,2-PROPANEDIOL

A solution of 1,2-propanediol (1.0 M), toluene (0.1 M) and {[Cp*Ru(CO)$_2$]$_2$(μ-H)}$^+$ OTf$^-$ (0.005 M) in sulfolane (50 mL) was placed into the glass liner of a Parr Mini-Reactor (300 mL capacity). HOTf (0.133 mL, 0.0015 mol) was added, and the reactor was sealed, and flushed twice with H$_2$, before pressurizing to 750 psi H$_2$ (5.2 MPa). The reaction was heated to 110° C. and samples were periodically removed and quantitatively analyzed by GC. After 48 hours, 0.214 M (21%) of the 1,2-propanediol remained, and the concentrations and yields of hydrogenated products were n-propanol (0.44 M, 44%), di-n-propyl ether (0.043 M, 8%), and propylene glycol propyl ether (0.14 M, 14%). Note that the di-n-propyl ether is considered as two hydrogenation equivalents, since it requires two equivalents of n-propanol to produce one equivalent of di-n-propyl ether. Therefore, the total yield of hydrogenation equivalents from this experiment indicated 66 turnovers (66% yield).

EXAMPLE 2

DEHYDROXYLATION OF 1,2-PROPANEDIOL AT HIGHER ACID CONCENTRATION

Using the general procedure described above, a solution of 1,2-propanediol (1.0 M), toluene (0.1 M) and {[Cp*Ru(CO)$_2$]$_2$(μ-H)}$^+$ OTf$^-$ (0.005 M) in sulfolane (50 mL) was placed into the glass liner of a Parr Mini-reactor (300 mL capacity). HOTf (0.266 mL, 0.0030 mol) was added to the solution in the autoclave. The reactor was sealed under 750 psi (5.2 MPa) H$_2$. Samples were periodically withdrawn for analysis. After 51 hours, 0.067 M (7%) of the 1,2-propanediol remained, and the concentrations and yields of hydrogenated products were n-propanol (0.54 M, 54%), di-n-propyl ether (0.079 M, 16%), and propylene glycol propyl ether (0.10 M, 10%). The total yield of hydrogenation equivalents from this experiment indicated 80 turnovers (80% yield).

EXAMPLE 3

DEHYDROXYLATION OF 1,2-PROPANEDIOL AT LOWER ACID CONCENTRATION

The procedure described in Example 2 was used. The only change was that the amount of HOTf added to the solution in the autoclave was 0.026 mL (0.0003 mol). After 46 hours, 0.58 M (58%) of the 1,2-propanediol remained, and the concentrations and yields of hydrogenated products were n-propanol (0.091 M, 9%), di-n-propyl ether (0.052 M, 1%), and propylene glycol propyl ether (0.11 M, 11%). The total yield of hydrogenation equivalents from this experiment indicated 21 turnovers (21% yield).

FIG. 1 shows the time profile of the reaction from Examples 1–3 above, and summarizes the dependence of the reaction on the concentration of HOTf ([HOTf]).

EXAMPLE 4

DEHYDROXYLATION OF 1,2-PROPANEDIOL AT HIGHER CATALYST CONCENTRATION

Using the general procedure described above, a solution of 1,2-propanediol (1.0 M), toluene (0.1 M) and {[Cp*Ru(CO)$_2$]$_2$($\mu$-H)}$^+$ OTf$^-$ (0.010 M) in sulfolane (50 mL) was placed into the glass liner of a Parr Mini-Reactor (300 mL capacity). HOTf (0.265 mL, 0.0030 mol) was added, and the reactor was sealed under hydrogen gas at 750 psi (5.2 MPa). Samples were periodically withdrawn for analysis. After 47 hours, 0.037 M (4%) of the 1,2-propanediol remained, and the concentrations and yields of hydrogenated products were n-propanol (0.51 M, 51%), di-n-propyl ether (0.078 M, 16%), propylene glycol propyl ether (0.090 M, 9%), and propylene glycol di-propyl ether (0.032 M, 6%). The total yield of hydrogenation equivalents from this experiment was thus 41 turnovers (82% yield).

EXAMPLE 5

DEHYDROXYLATION OF 1,2-PROPANEDIOL AT LOWER CATALYST CONCENTRATION

Using the general procedure described above, a solution of 1,2-propanediol (1.0 M), toluene (0.1 M) and {[Cp*Ru(CO)$_2$]$_2$($\mu$-H)}$^+$ OTf$^-$ (0.0025 M) in sulfolane (50 mL) was placed into the glass liner of a Parr Mini-Reactor (300 mL capacity). HOTf (0.0661 mL, 0.0030 mol) was added, and the reactor was sealed under hydrogen gas at 750 psi (5.2 MPa). Samples were periodically withdrawn for analysis. After 33 hours, 0.80 M (80%) of the 1,2-propanediol remained, and the concentrations and yields of hydrogenated products were n-propanol (0.050 M, 5%) and propylene glycol propyl ether (0.087 M, 9%). The total yield of hydrogenation equivalents from this experiment indicated 28 catalyst turnovers (14%).

Figure 2:
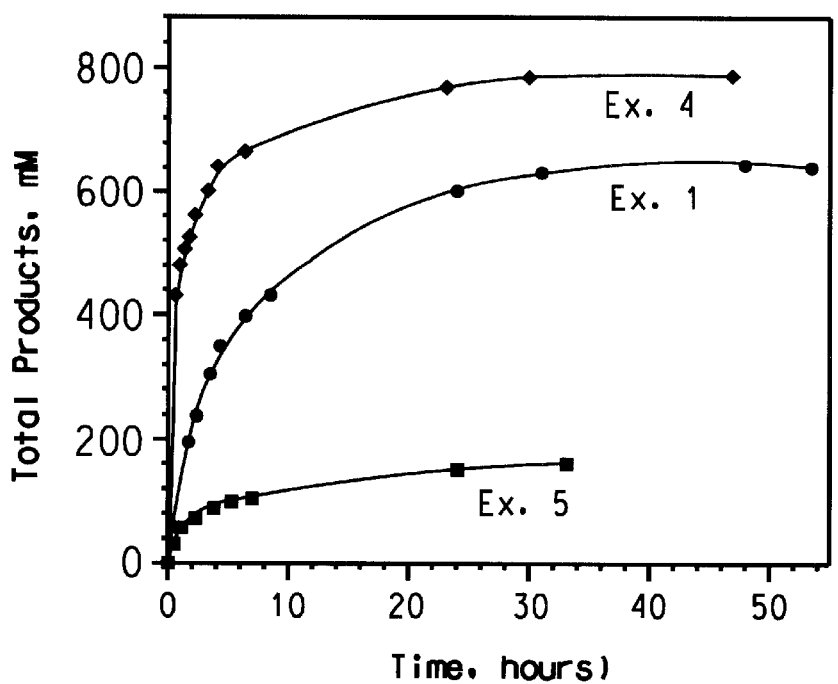
FIG. 2 is a graph showing the time or reaction vs. concentration of $Ru_2$.

FIG. 2 shows the time profile of the reaction from Examples 1, 4 and 5 above, and summarizes the dependence of the reaction on the catalyst concentration.

EXAMPLE 6

DEHYDROXYLATION OF 1-PHENYL-1,2-ETHANEDIOL

A solution of CD$_2$Cl$_2$ (1 mL) containing 1-phenyl-1,2-ethanediol (0.0138 g, 0.10 M) and {[Cp*Ru(CO)$_2$]$_2$($\mu$-H)}$^+$ OTf$^-$ (0.015 g, 0.02 M) was sealed under H$_2$ (45 psi, 0.31 MPa). The solution was heated at 85° C. for 48 hours. After 48 hours, analysis by $^1$H nuclear magnetic resonance (NMR) spectroscopy indicated the formation of 2-phenylethanol (estimated yield >85% by NMR). Note also that this reaction was conducted without any added acid.

EXAMPLE 7

DEHYDROXYLATION OF GLYCEROL

A solution of glycerol (1.0 M), toluene (0.1 M) and {[Cp*Ru(CO)$_2$]$_2$($\mu$-H)}$^+$ OTf$^-$ (0.01 M) in sulfolane (25 mL) was placed into the glass liner of a Parr Mini-Reactor (300 mL capacity). HOTf (0.266 mL, 0.003 mol) was added. The reactor was sealed, flushed twice with H$_2$, and pressurized to 750 psi hydrogen gas (5.2 MPa). The reaction was heated to 110° C. After 19 hours, the following dehydroxylated products were detected by GC analysis: n-propanol (0.057 M), di-n-propyl ether (0.0027 M) and 1,3-propanediol (0.046 M).

EXAMPLE 8

DEHYDROXYLATION OF 1,2-PROPANEDIOL BY (Cp$^{Bu^t}_2$)Ru(CO)$_2$H

A solution of 1,2-propanediol (0.94 M), toluene (0.1 M) and (Cp$^{Bu^t}_2$)Ru(CO)$_2$H (0.084 g, 0.250 mmol) in sulfolane (25 mL) was placed into the glass liner of a Parr Mini-Reactor (300 mL capacity). HOTf (122 $\mu$L, 1.38 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 50 hours, 0.081 M (8%) of the 1,2-propanediol remained, and the concentrations and yields of hydrogenated products were n-propanol (0.44 M, 46%), di-n-propyl ether (0.058 M, 6%), and propylene glycol propyl ether (0.18 M, 18%). The total yield of hydrogenation equivalents from this experiment indicated 78 catalyst turnovers (83% yield).

EXAMPLE 9

DEHYDROXYLATION OF 1,2-PROPANEDIOL BY (Cp$^{Pr^i}_4$)Ru(CO)$_2$H

A solution of 1,2-propanediol (1.0 M), toluene (0.1 M) and (Cp$^{Pr^i}_4$)Ru(CO)$_2$H (0.157 g, 0.401 mmol) in sulfolane (40 mL) was placed into the glass liner of a Parr Mini-Reactor (300 mL capacity). HOTf (195 $\mu$L, 2.20 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 96 hours, 0.48 M (48%) of the 1,2-propanediol remained, and the concentrations and yields of hydrogenated products were n-propanol (0.14 M, 14%), di-n-propyl ether (0.016 M, 2%), and propylene glycol propyl ether (0.16 M, 16%). Note that the di-n-propyl ether is considered as two hydrogenation equivalents, since it requires two equivalents of n-propanol to produce one equivalent of di-n-propyl ether. Therefore, the total yield of hydrogenation equivalents from this experiment indicated 34 catalyst turnovers (34% yield).

EXAMPLE 10

DEHYDROXYLATION OF 1,2-PROPANEDIOL BY (Cp$^{Bz}_5$)Ru(CO)$_2$H

A solution of 1,2-propanediol (1.0 M), toluene (0.1 M) and (Cp$^{Bz}_5$)Ru(CO)$_2$H (0.168 g, 0.250 mmol) in sulfolane (25 mL) was placed into the glass liner of a Parr Mini-Reactor (300 mL capacity). HOTf (122 $\mu$L, 1.37 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 74 hours, 0.55 M (55%) of the 1,2-propanediol remained, and the concentrations and yields of hydrogenated products were n-propanol (0.17 M, 17%), di-n-propyl ether (0.015 M, 1.5%), and propylene glycol propyl ether (0.18 M, 18%).

Therefore, the total yield of hydrogenation equivalents from this experiment indicated 38 catalyst turnovers (38% yield).

EXAMPLE 11

DEHYDROXYLATION OF 1,2-PROPANEDIOL BY {[Ind(Me$_3$)]Ru(CO)$_2$}$_2$

A solution of 1,2-propanediol (1.0 M), toluene (0.1 M) and {[Ind(Me$_3$)]Ru(CO)$_2$}$_2$ (0.126 g, 0.200 mmol) in sulfolane (40 mL) was placed into the glass liner of a Parr Mini-Reactor (300 mL capacity). HOTf (230 µL, 2.60 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 96 hours, 0.15 M (16%) of the 1,2-propanediol remained, and the concentrations and yields of hydrogenated products were n-propanol (0.23 M, 23%), di-n-propyl ether (0.009 M, 1%), and propylene glycol propyl ether (0.07 M, 7%). Therefore, the total yield of hydrogenation equivalents from this experiment indicated 32 catalyst turnovers (32% yield).

EXAMPLE 12

DEHYDROXYLATION OF 1,2-PROPANEDIOL BY Tp*Ru(COD)H

A solution of 1,2-propanediol (1.0 M), toluene (0.1 M) and Tp*Ru(COD)H (0.203 g, 0.400 mmol) in sulfolane (40 mL) was placed into the glass liner of a Parr Mini-Reactor (300 mL capacity). HOTf (195 µL, 2.20 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 96 hours, 0.62 M (62%) of the 1,2-propanediol remained, and the concentrations and yields of hydrogenated products were n-propanol (0.043 M, 4%), di-n-propyl ether (0 M, 0%), and propylene glycol propyl ether (0 M, 0%). Therefore, the total yield of hydrogenation equivalents from this experiment indicated 4 catalyst turnovers (4% yield).

EXAMPLE 13

DEHYDROXYLATION OF 1,2-PROPANEDIOL BY Tp*Ru(CO)$_2$H

A solution of 1,2-propanediol (1.0 M), toluene (0.1 M) and Tp*Ru(CO)$_2$H (0.182 g, 0.400 mmol) in sulfolane (40 mL) was placed into the glass liner of a Parr Mini-Reactor (300 mL capacity). HOTf (195 µL, 2.20 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 95 hours, 0.19 M (19%) of the 1,2-propanediol remained, and the concentrations and yields of hydrogenated products were n-propanol (0.32 M, 32%), di-n-propyl ether (0.027 M, 3%), and propylene glycol propyl ether (0.09 M, 9%). Therefore, the total yield of hydrogenation equivalents from this experiment indicated 47 catalyst turnovers (47% yield).

EXAMPLE 14

DEHYDROXYLATION OF 1,2-PROPANEDIOL BY {(CpSiMe$_2$)$_2$Ru$_2$(CO)$_4$(µ-H)}BF$_4$

A solution of 1,2-propanediol (1.0 M), toluene (0.1 M) and {(CpSiMe$_2$)$_2$Ru$_2$(CO)$_4$(µ-H)}BF$_4$ (0.081 g, 0.125 mmol) in sulfolane (25 mL) was placed into the glass liner of a Parr Mini-Reactor (300 mL capacity). HOTf (133 µL, 1.50 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 71 hours, 0.66 M (66%) of the 1,2-propanediol remained, and the concentrations and yields of hydrogenated products were n-propanol (0.015 M, 1.5%), di-n-propyl ether (0 M, 0%), and propylene glycol propyl ether (0.011 M, 1%). Therefore, the total yield of hydrogenation equivalents from this experiment indicated 2.6 catalyst turnovers (2.6% yield).

EXAMPLE 15

DEHYDROXYLATION OF 1,2-PROPANEDIOL BY Cp*Ru(CO)(PMe$_3$)H

A solution of 1,2-propanediol (1.0 M), toluene (0.1 M) and Cp*Ru(CO)(PMe$_3$)H (0.137 g, 0.400 mmol) in sulfolane (40 mL) was placed into the glass liner of a Parr Mini-Reactor (300 mL capacity). HOTf (195 µL, 2.20 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 92 hours, 0.31 M (32%) of the 1,2-propanediol remained, and the concentrations and yields of hydrogenated products were n-propanol (0.33 M, 33%), di-n-propyl ether (0.015 M, 1.5%), and propylene glycol propyl ether (0.06 M, 6%). Therefore, the total yield of hydrogenation equivalents from this experiment indicated 42 catalyst turnovers (42% yield).

EXAMPLE 16

DEHYDROXYLATION OF 1,2-PROPANEDIOL BY [(Cp*Ru(CO)$_2$)$_2$(µ-H)]OTf

A solution of 1,2-propanediol (1.0 M), toluene (0.1 M) and [(Cp*Ru(CO)$_2$)$_2$(µ-H)]OTf (0.147 g, 0.200 mmol) in sulfolane (40 mL) was placed into the glass liner of a Parr Mini-Reactor (300 mL capacity). HOTf (213 µL, 2.40 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 78 hours, 0.13 M (13%) of the 1,2-propanediol remained, and the concentrations and yields of hydrogenated products were n-propanol (0.46 M, 46%), di-n-propyl ether (0.061 M, 6%), and propylene glycol propyl ether (0.12 M, 12%). Therefore, the total yield of hydrogenation equivalents from this experiment indicated 72 catalyst turnovers (72% yield).

EXAMPLE 17

DEHYDROXYLATION OF 1,2-PROPANEDIOL BY CpRu[P(OPh)$_3$]$_2$H

A solution of 1,2-propanediol (1.0 M), toluene (0.1 M) and CpRu[P(OPh)$_3$]$_2$H (0.197 g, 0.250 mmol) in sulfolane (25 mL) was placed into the glass liner of a Parr Mini-Reactor (300 mL capacity). HOTf (122 µL, 1.37 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 98 hours, 0.55 M (55%) of the 1,2-propanediol remained, and the concentrations and yields of hydrogenated products were n-propanol (0.21 M, 21%), di-n-propyl ether (0 M, 0%), and propylene glycol propyl ether (0.04 M, 4%). Therefore, the total yield of hydrogenation equivalents from this experiment indicated 25 catalyst turnovers (25% yield).

EXAMPLE 18

DEHYDROXYLATION OF 1,2-PROPANEDIOL BY CpRu(CO)[P(OPh)$_3$]H

A solution of 1,2-propanediol (1.0 M), toluene (0.1 M) and CpRu(CO)[P(OPh)$_3$]H (0.126 g, 0.250 mmol) in sulfolane (25 mL) was placed into the glass liner of a Parr Mini-Reactor (300 mL capacity). HOTf (122 µL, 1.37 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 48 hours, 0.53 M (53%) of the 1,2-propanediol remained, and the concentrations and yields of hydrogenated products were n-propanol (0.13 M, 13%), di-n-propyl ether (0.012 M, 1%), and propylene glycol propyl ether (0.18 M, 18%). Therefore, the total yield of hydrogenation equivalents from this experiment indicated 35 catalyst turnovers (35% yield).

EXAMPLE 19

DEHYDROXYLATION OF 1,2-PROPANEDIOL BY CpRu(CO)[P(Ph—F)$_3$]H

A solution of 1,2-propanediol (1.0 M), toluene (0.1 M) and CpRu(CO)[P(Ph—F)$_3$]H (0.128 g, 0.250 mmol) in sulfolane (25 mL) was placed into the glass liner of a Parr Mini-Reactor (300 mL capacity). HOTf (122 µL, 1.37 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 94 hours, 0.03 M (3%) of the 1,2-propanediol remained, and the concentrations and yields of hydrogenated products were n-propanol (0.46 M, 46%), di-n-propyl ether (0.053 M, 5%), and propylene glycol propyl ether (0.06 M, 6%). Therefore, the total yield of hydrogenation equivalents from this experiment indicated 62 catalyst turnovers (62% yield).

EXAMPLE 20

DEHYDROXYLATION OF 1,2-PROPANEDIOL BY CpRu(CO)[PCy$_3$]H

A solution of 1,2-propanediol (1.0 M), toluene (0.1 M) and CpRu(CO)[P(cyclohexyl)$_3$]H (0.119 g, 0.250 mmol) in sulfolane (25 mL) was placed into the glass liner of a Parr Mini-Reactor (300 mL capacity). HOTf (122 µL, 1.37 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 96 hours, 0.03 M (3%) of the 1,2-propanediol remained, and the concentrations and yields of hydrogenated products were n-propanol (0.47 M, 47%), di-n-propyl ether (0.045 M, 4.5%), and propylene glycol propyl ether (0.08 M, 8%). Therefore, the total yield of hydrogenation equivalents from this experiment indicated 66 catalyst turnovers (66% yield).

EXAMPLE 21

DEHYDROXYLATION OF 1,2-PROPANEDIOL BY CpRu(CO)[PMe$_3$]H

A solution of 1,2-propanediol (1.0 M), toluene (0.1 M) and CpRu(CO)[PMe$_3$]H (0.109 g, 0.400 mmol) in sulfolane (40 mL) was placed into the glass liner of a Parr Mini-Reactor (300 mL capacity). HOTf (195 µL, 2.20 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 96 hours, 0.16 M (16%) of the 1,2-propanediol remained, and the concentrations and yields of hydrogenated products were n-propanol (0.45 M, 45%), di-n-propyl ether (0.039 M, 4%), and propylene glycol propyl ether (0.08 M, 8%). Therefore, the total yield of hydrogenation equivalents from this experiment indicated 61 catalyst turnovers (61% yield).

EXAMPLE 22

DEHYDROXYLATION OF 1,2-PROPANEDIOL BY [(CpRu(CO)$_2$)$_2$(µ-H)]OTf

A solution of 1,2-propanediol (1.0 M), toluene (0.1 M) and [(CpRu(CO)$_2$)$_2$(µ-H)]OTf (0.119 g, 0.200 mmol) in sulfolane (40 mL) was placed into the glass liner of a Parr Mini-Reactor (300 mL capacity). HOTf (213 µL, 2.40 mmol) was added, and the reactor was sealed, and flushed five times with H$_2$, before pressurizing to 750 psi H$_2$ (5.2 MPa). The reaction was heated to 110° C. and samples were periodically removed and quantitatively analyzed by GC. After 96 hours, 0.17 M (17%) of the 1,2-propanediol remained, and the concentrations and yields of hydrogenated products were n-propanol (0.19 M, 19%), di-n-propyl ether (0.047 M, 5%), and propylene glycol propyl ether (0.17 M, 17%). Therefore, the total yield of hydrogenation equivalents from this experiment indicated 49 catalyst turnovers (49% yield).

What is claimed is:

1. A process for the selective dehydroxylation of a secondary alcohol, comprising the step of contacting a secondary alcohol with hydrogen in the presence of a catalytically effective amount of a catalyst precursor having the formula {[CpRu(CO)$_2$]$_2$(µ-H)}$^+$Q$^-$ or {[CpRu(CO)(PR'$_3$)]$_2$(µ-H)}$^+$Q$^-$ or {[ZRu(L)]$_2$(µ-H)}$^+$Q$^-$, wherein Q$^-$ is a non-coordinating or weakly coordinating nonreactive anion;

Cp is η$^5$—C$_5$R$_5$ wherein R is selected from the group consisting of hydrogen and substituted and unsubstituted C$_1$–C$_{18}$ alkyl groups, where any two adjacent R groups can together form a ring;

R' is selected from the group consisting of hydrogen, alkyl, aryl, alkoxy and aryloxy;

Z is hydridotris(3,5-dimethylpyrazolyl)borate or hydrocarbyl hydridotris(3,5-dimethylpyrazolyl)borate; and L is (CO)$_2$ or 1,5-cyclooctadiene;

and, wherein the secondary alcohol has a secondary alcohol functionality.

2. The process according to claim 1 wherein the secondary alcohol has a primary alcohol functionality in addition to the secondary alcohol functionality.

3. The process according to claim 1 wherein Q$^-$ is selected from the group consisting of OSO$_2$CF$_3$— and BF$_4$—.

4. The process according to claim 1 wherein the secondary alcohol is a substituted linear, branched or cyclic saturated C$_2$–C$_{18}$ compound.

5. The process according to claim 1 wherein the secondary alcohol is selected from the group consisting of 1,2-propanediol, glycerol and 1-phenyl-1,2ethanediol.

6. The process according to claim 3 wherein:
  R is hydrogen, methyl, i-propyl, benzyl, dimethylsilyl, or together with the cyclopentadienyl group forms an indenyl ring;
  R' is methyl, phenoxy, p-fluorophenyl, or cyclohexyl; and
  Z is hydridotris(3,5-dimethylpyrazolyl)borate.

7. The process according to claim 1, wherein the secondary alcohol and the hydrogen are contacted in the presence of the catalyst precursor and in the presence of $H^+Q^-$.

8. The process according to claim 7 wherein the $H^+Q^-$ is $HOSO_2CF_3$.

9. The process according to claim 1 wherein the process is conducted at a temperature of about 100° C. to about 110° C.

10. The process according to claim 1 wherein the process is conducted at a pressure of about 0.1 MPa to 5.5 MPa.

11. The process according to claim 1 wherein the process is conducted in sulfolane solvent.

* * * * *